United States Patent [19]

Skinner

[11] Patent Number: 5,084,024
[45] Date of Patent: Jan. 28, 1992

[54] CATHETER AND METHOD FOR RELIEVING CATHETER STRESS

[75] Inventor: Steven M. Skinner, Billerica, Mass.

[73] Assignee: Thermedics, Inc., Woburn, Mass.

[21] Appl. No.: 447,570

[22] Filed: Dec. 7, 1989

[51] Int. Cl.$^5$ ............................................. A61M 5/32
[52] U.S. Cl. .................................................... 604/175
[58] Field of Search .............................. 604/280-283, 604/264, 8, 175, 114, 93, 174; 128/DIG. 26; 606/32

[56] References Cited

U.S. PATENT DOCUMENTS

| | | | |
|---|---|---|---|
| 1,998,225 | 4/1935 | Dow | 128/DIG. 26 |
| 3,612,038 | 10/1971 | Halligan | 604/281 |
| 3,890,977 | 6/1975 | Wilson | 604/281 |
| 4,016,884 | 4/1977 | Kwan-Gett | 604/175 |
| 4,038,519 | 7/1977 | Foucras | 604/114 |
| 4,397,641 | 8/1983 | Jacobs | 128/DIG. 26 |
| 4,419,094 | 12/1983 | Patel . | |
| 4,496,352 | 1/1985 | Soika . | |
| 4,579,120 | 4/1986 | MacGregor . | |
| 4,643,716 | 2/1987 | Drach | 604/281 |
| 4,645,492 | 2/1987 | Weeks | 120/DIG. 26 |
| 4,687,471 | 8/1987 | Twardowski et al. | 604/280 |
| 4,738,667 | 4/1988 | Galloway | 604/281 |
| 4,795,439 | 1/1989 | Gzest | 604/280 |
| 4,810,246 | 3/1989 | Frisch et al. | 604/175 |
| 4,834,725 | 5/1989 | Iwatschenko | 604/281 |
| 4,874,380 | 10/1989 | Hesketh | 128/DIG. 26 |
| 4,886,502 | 12/1989 | Poirier et al. . | |
| 4,935,004 | 6/1990 | Cruz | 604/281 |

FOREIGN PATENT DOCUMENTS

| | | |
|---|---|---|
| 0081724 | 11/1982 | European Pat. Off. . |
| 8606282 | 4/1986 | PCT Int'l Appl. . |
| 894164 | 7/1960 | United Kingdom . |
| 1499520 | 2/1975 | United Kingdom . |

Primary Examiner—C. Fred Rosenbaum
Assistant Examiner—Mark Backelman
Attorney, Agent, or Firm—Lorusso & Loud

[57] ABSTRACT

An improved catheter and catheter system for long term implantation in a patient through a percutaneous access device are provided. The improved catheter has a loop in an external lead portion of the catheter which reduces bending, kinking, and cracking of the catheter and which reduces stress on the catheter and on the percutaneous access device as well. The system employs multiple catheters, each catheter having a loop to reduce stress. Each of the catheters of the system may have a single lumen or multiple lumens. A method of relieving stress at an external lead portion of a single or multi-lumen catheter is also provided.

32 Claims, 3 Drawing Sheets

CATHETER AND METHOD FOR RELIEVING CATHETER STRESS

BACKGROUND OF THE INVENTION

1. Field of the Invention

This invention relates to catheters used for the introduction of fluids or electrical leads into a patient. More particularly, it relates to an improved catheter and method for relieving stress at an external lead portion of a catheter, which is inserted into a patient through an implanted percutaneous access device.

2. Prior Art

Various flexible percutaneous leads have been employed in the past which extend into the body of a patient and exit the patient's body at some selected location on the body. Such leads include, for example, electrically conductive temporary or permanent heart pacer leads and neural stimulator leads for stimulating the nervous system of the patient. One end of such lead, the end in the patient's body, is located at the location which is to be stimulated—for example, the myocardium or the epidural space surrounding the spinal cord. The conductive lead is connected to a stimulator which may be carried on the exterior of the patient's body. The stimulator produces electrical signals which are transmitted through the lead to stimulate the tissue which is to be stimulated deep within the patient's body.

Problems have been encountered with such percutaneous leads which have been fixed in place at the location at which the lead exits the skin. One such problem is that the strain which may be imparted to the lead during patient activity are transmitted to the exit location and may cause movement or displacement of the lead and even tearing of skin with attendant patient trauma. U.S. Pat. No. 4,579,120, entitled "Strain Relief for Percutaneous Lead" teaches a method and member for anchoring and relieving the strain on such leads. The stress toward which that invention is directed is stress to the patient at the exit site, most particularly stress caused by the movement of a sutured percutaneous lead.

Whereas the function of electrically conductive leads is not inhibited by bending and kinking, catheters which are used to transmit fluids have an internal lumen which must allow unimpeded fluid flow. Cracks in a catheter which transmits fluid will allow fluid to leak out and air to leak in; similar cracks in electrical leads are much less problematic. Accordingly, the disclosure of U.S. Pat. No. 4,579,120 is much less useful for catheters leads because no method is provided for preserving the integrity of the inner lumen of a hollow catheter.

Other percutaneous access devices (PADs) are known which are more specifically designed for catheter support. Nevertheless, such PADs alone are not adequately suited for preventing damage to known catheters, or even for preventing compromise of the integrity of internal catheter lumens, because catheter damage often occurs at the leading external edge of the catheter, beyond the PAD itself. The weight of the catheter or external forces act on the catheter and can cause the catheter to place strain on the PAD. Such forces are likely to lead to bending, kinking, or cracking of the catheter near the entry site impeding fluid flow, and can also lead to injury to the patient.

Some solutions to the above-discussed catheter problems have been proposed. It is known, for example, to place an approximately ninety degree bend in catheters to alleviate strain. U.S. Pat. No. 4,419,094 entitled "Suprapubic Catheter System" discloses a catheter with a curve in it. The catheter is held in place in a fixed direction and in a curved conformation by means of a plate which is attached to a second plate which, in turn, may be sutured or taped to the patient. It would, of course, be preferable to have a catheter for use with a PAD which does not require additional sutures o adhesives, which does not require a plate assembly, and which is capable of being adapted for use in any direction. Such a catheter is disclosed in U.S. Pat. No. 4,886,502 entitled "Peritoneal Access Catheter", the teaching of which is incorporated herein by reference, in which a flexible bellows section was implemented to allow a catheter to adopt up to a ninety degree bend in any direction.

SUMMARY OF THE PRESENT INVENTION

An omnidirectional catheter having an improved leading end, and a method of relieving stress on a catheter and a percutaneous access device are provided. To relieve stress, the catheter has a pre-formed loop at its external lead portion which maintains a large radius of curvature at all points external to the body of the patient. This prevents bends and kinks from forming in the catheter which might impede fluid flow or cause the catheter to crack. It also relieves stress on the percutaneous access device. The method of relieving stress involves forming a loop in an external lead portion of a catheter which is to be inserted through a percutaneous access device which is implanted in a patient.

Accordingly, it is an object of the present invention to provide a catheter which is capable of being implanted in a patient through a percutaneous access device for long term fluid delivery without placing undue pressure on the percutaneous access device.

It is another object of the present invention to provide a catheter which is capable of preventing compromise of its internal lumen during long term implantation in a patient through a percutaneous access device.

It is yet another object of the present invention to provide a catheter which may be implanted in a patient through a percutaneous access device for long term fluid delivery which is capable of maintaining a large radius of curvature at all points external to the patient's body without the aid of any unwieldy support structure.

It is still another object of the present invention to provide a method for preserving the integrity of the internal lumen of any catheter which is to be implanted in a patient through a percutaneous access device.

It is yet another object of the present invention to provide a catheter may be implanted in a patient through a percutaneous access device for long term access with electrical conductors.

These and other objects and advantages of the present invention will be more clearly understood from the Description of the Preferred Embodiments made with reference to the drawings in which like numerals refer to like parts.

DESCRIPTION OF THE PREFERRED EMBODIMENTS

At the outset, the invention is described in its broadest overall aspects, with a more detailed description following. In its broadest overall aspects, the present invention is an improved catheter, and a method for relieving stress at an exit site of a catheter. It is anticipated that the catheter of the present invention, or any catheter constructed according to the method of the invention, will be used in conjunction with a percutaneous access device (PAD). The catheter may be used with any of the known PADs; one such suitable PAD is the DERMAPORT ® device available from Thermedics, Inc. of Woburn, Mass. Catheters which are used in this invention in conjunction with PADs may be of essentially two varieties: (1) a single tube used for the transmission of fluids or electricity, or (2) at least two tubes hermetically sealed from one another for the transmission of fluids or electricity. Either variety of catheter may be used in this invention. It is possible to use a single tube containing at least two lumens hermetically sealed from one another as well. In that case, the single tube will be composed from two parts for ease of construction; when implanted, the first segment extends outward from the PAD and the second segment inward, with the two segments sealed together at a junction within the PAD. The use of multi-lumen catheters is fully described in copending U.S. application Ser. No. 399,160 to Poirier et al., the teaching of which is incorporated herein by reference. The use of a single or multi-lumen catheter with a PAD is described fully in that reference as well.

The improved catheter has a loop formed at an external lead portion. The method for relieving stress near the exit site of a catheter involves forming and fixing a loop in the catheter prior to implantation of the catheter.

Figure 1:
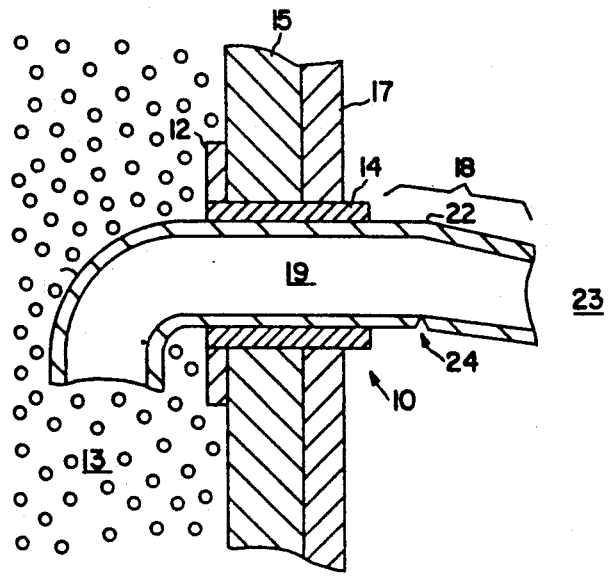
FIG. 1 is a side view of a portion of a catheter of the prior art in a percutaneous access device in-vivo showing a kink and a crack in the external lead portion.

With reference to FIG. 1, a PAD 10 is shown in conjunction with a catheter 16 of the prior art. In use, the skirt 12 of the PAD 10 is embedded in subcutaneous tissue 13 and the neck 14 of the PAD 10 extends through the dermal layer 15 and the epidermal layer 17 of the skin to the surface of the body. The catheter 16 has a leading or subcutaneous or distal end (not shown) which is inserted into and through a bore 19 of the neck 14 of the PAD 10 to emerge from the opposite end of the PAD 10, the bore 19 being just wide enough to accommodate the catheter 16. The distal end of the catheter is inserted into a cavity, duct or vessel depending on the particular application for which the catheter 16 is used and will remain in fluid communication therewith.

The trailing or external or proximal end (not shown) of the catheter 16 in some cases will be attached to and in fluid communication with a suitable vehicle for carrying the fluids to be administered. The particular fluids to be administered will vary with the application for which the catheter 16 is used, but may include drug solutions, saline solutions, and nutrient solutions, among others. Prior art catheters are used for the withdrawal of fluids, such as blood, from the patient as well.

Particularly shown in FIG. 1 is the external lead portion 18 of the catheter 16 at the point just external to the PAD 10 at the site at which the catheter 16 emerges from the patient. As shown in that figure, the catheter 16 emerges in a substantial straight line normal to the skirt 12 and in accordance with the direction of the neck 14 of the PAD 10, and is then bent at a ninety degree angle parallel to the skirt 12 and the patient's epidermis 17. Also shown in that figure is the effect of external forces which tend to pull the catheter away from the patient's epidermis 17; that is, movement and pulling of the catheter 16 in the area 23 near the bend 22 has led to the formation of a crack 24 in the catheter 16. The crack 24 destroys the integrity of the internal lumen of the catheter 16 and may lead to fluid loss or the addition of air to the fluid administered, either of which can be dangerous to a patient.

Figure 2:
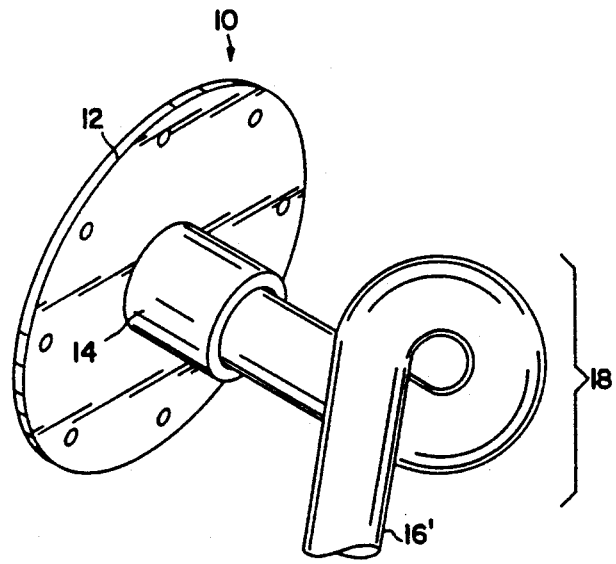
FIG. 2 is a perspective view of a portion of the catheter of the present invention in a percutaneous access device ex-vivo showing the loop configuration of the external lead portion.

With reference now to FIG. 2, the external lead portion 18' of the catheter 16' of the present invention is shown in a PAD 10 ex-vivo. The distal and proximal ends (not shown) of the catheter 16' function according to the description given above for prior art catheters, it being understood that the catheter 16' may carry electrical wires instead of fluids if desired. The catheter 16' of the present invention may be used for the withdrawal of fluids from a patient as can prior art catheters, but such applications of catheters are usually not for such long time periods (e.g., several months) as might lead to the problems overcome by the present invention. The external lead portion 18' is in the shape of a loop. Such a configuration maintains a large radius of curvature in the catheter 16' at all points external to the body of the patient. This configuration, therefore, reduces kinking and bending in the catheter 16' which might impede the fluid flow through the internal lumen of the catheter 16'. The absence of bends and kinks, moreover, reduces the formation of cracks which might compromise the integrity of the lumen. The loop 18' is configured such that fluid flow through the internal lumen of the catheter 16' is not constricted, yet stress is relieved. Thus, the diameter of the circular projection defined by the loop 18' may vary. The radius of curvature is dependent upon the overall dimensions of the catheter 16', but in the preferred configuration the catheter has an inner diameter of 0.104" and an outer diameter of 0.165", and the radius of curvature of the loop 18' is at least 3/16". The loop 18' encircles the neck 14 of the PAD 10 and may be positioned so that the remainder of the catheter may assume any direction. FIG. 2 shows a catheter having a 180° loop 18'. A loop must have greater than a 90° arc, but any arc greater than 90° is satisfactory for accomplishing the goals of the present invention. In addition to overcoming the problems associated with bends, the catheter 16' reduces stress to the PAD 10. This design reduces the stress by distributing the force over a much larger area encompassed by the loop 18'.

Thus, the force transmitted to the PAD 10 and the stress at the bend are both greatly reduced.

The loop configuration of the external lead portion 18' may be formed in any of many different ways. In a preferred embodiment, the loop 18' is heat-set in a thermoplastic or thermoset catheter 16'. A suitable thermoplastic is TECOFLEX® EG-85A. manufactured by Thermedics Inc. of Woburn, Mass. A suitable thermoset material is Silicone manufactured by Dow Corning Corp. of Midland, Migh.

The catheter 16' of the present invention has been found to be better than known catheters for relieving stress and for ease of positioning.

Figure 3:
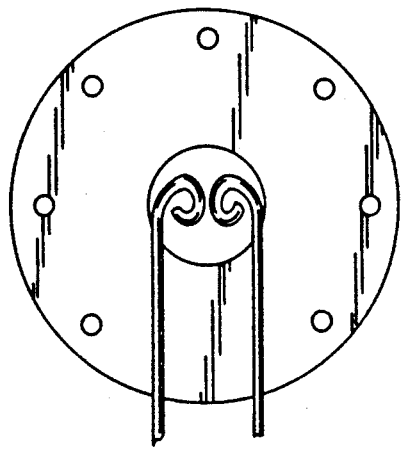
FIG. 3 is a plan view of an alternate embodiment of the present invention illustrating two or more conduits for carrying either fluid or electricity to or from a patient through a percutaneous access device.

In an alternate embodiment, shown in FIG. 3, it is possible to insert two catheters 16' of the present invention, each with a loop 18', simultaneously through a single PAD.

Figure 4:
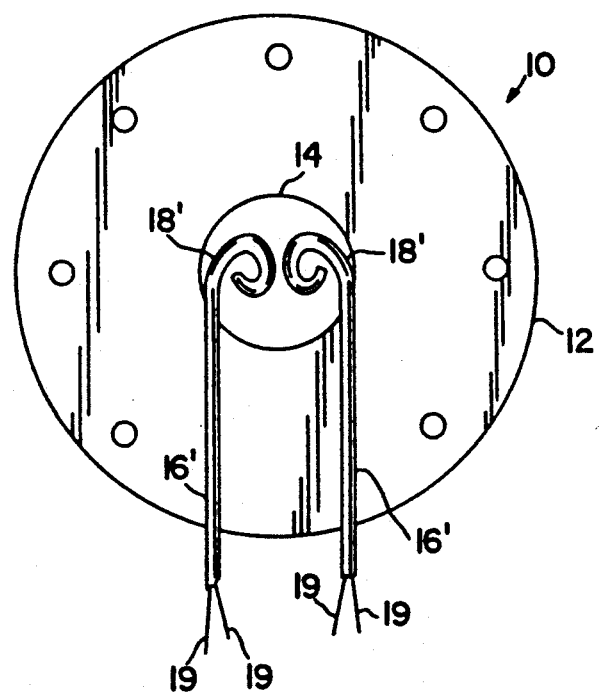
FIG. 4 is a plan view of an alternate embodiment of the present invention illustrating two or more conduits and electrical conductors running through them.

FIG. 4 illustrates the alternate embodiment of two catheters 16', each with a loop 18', simultaneously through a single PAD, and electrical conductors 19 through the catheters 16'. Of course, electrical conductors can be present in an embodiment utilizing one catheter through a PAD, or alternatively, in a multi-lumen catheter, through one lumen of such a catheter.

Figure 5:
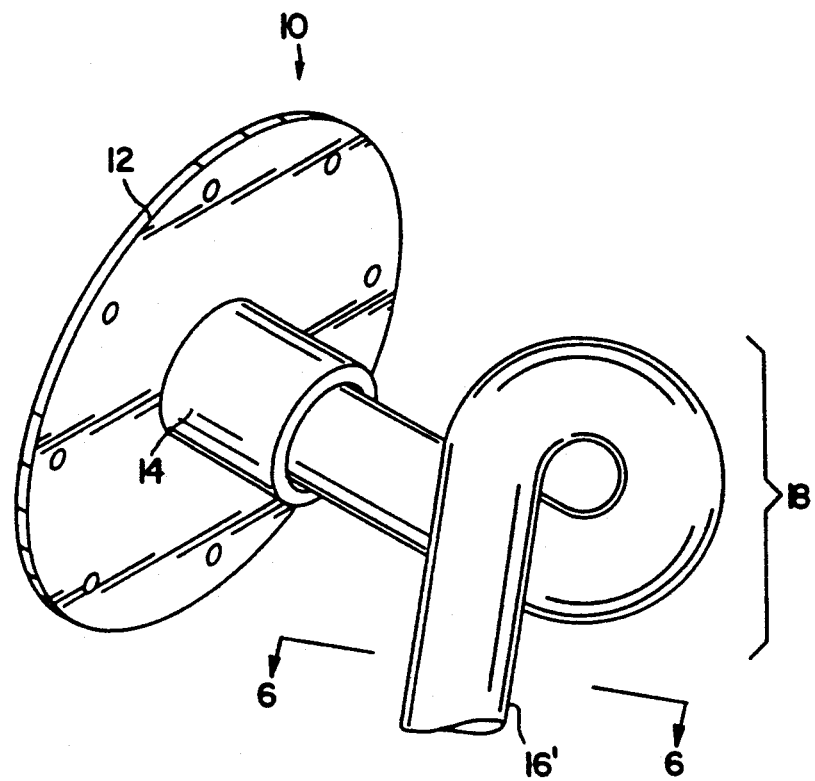
FIG. 5 is perspective view of a portion of an alternate embodiment of the catheter of the present invention, having a multi-lumen tube, the catheter positioned in a percutaneous access device ex-vivo and having the loop configuration of the external lead portion.
Figure 6:
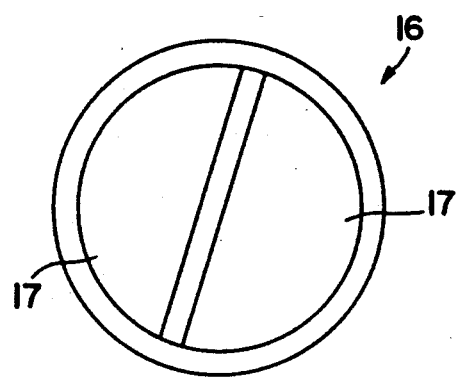
FIG. 6 is a cross sectional view, taken along the line 6—6 in FIG. 5 and illustrating the lumens of the multi-lumen catheter of this embodiment of the present invention.

In another alternate embodiment, a multi-lumen catheter can be used, as shown in FIGS. 5 and 6. One possible arrangement of the various lumens 17 is illustrated in FIG. 6. Of course, those skilled in the art will select a lumen arrangement to produce a catheter ideally suited for the specific application.

The method of the invention involves forming a loop in an external lead portion of a catheter which is to be inserted into a patient through a percutaneous access device which is implanted in the patient. The loop can be maintained in the catheter in any fashion that avoids kinks and bends in the catheter. In a preferred embodiment, the loop is heat-set in a catheter composed of TECOFLEX EG-85A thermoplastic polyurethane material using a mandrel which is sufficient to give the loop a radius of curvature of at least 3/16". A wire form is bent to the preferred configuration, and the tube is positioned on the form by passing the wire through the internal lumen of the tube. The catheter is then heatset by heating the wire and tube to a temperature of 110° C. for about one hour. The wire form and tube are then allowed to cool to room temperature and the wire is removed. If a multi-lumen catheter is desired, then a multi-wire mandrel is used, and one wire is passed through each lumen of the catheter.

The present invention may be embodied in other forms without departing from the spirit or essential characteristics thereof. The present embodiments are to be considered in all respects as illustrative and not restrictive, the scope of the invention being determined by the appended claims rather than the foregoing description, and there being no intention of excluding equivalents thereof. It is recognized that various modifications are possible when within the scope of the present invention as claimed.

I claim:

1. An improved system for the introduction of fluids or electrical leads to a patient, said system comprising:
   a percutaneous access device including a skirt for embedding in the subcutaneous tissue of the patient and a neck extending from the skirt for extending through the dermal and epidermal layers of the skin of the patient, said neck having a bore therethrough; and
   a catheter comprising a thermoset or thermoplastic tube defining an internal lumen, said tube having an outer diameter sized to permit insertion of the tube through said bore and having a proximal end for placement in the patient and a distal end located external to the patient when the catheter is in use, said tube also having a permanent loop with an arc of at least 90° toward its distal end at a portion of the catheter which is just external to the patient when the catheter is in place.

2. The improved system of claim 1 wherein said loop is heat-set.

3. The improved system of claim 1 wherein a remaining external portion of said tube, proximal to said external portion having said loop, may be oriented in any direction.

4. The improved system of claim 1 wherein said arc is at least 180°.

5. The improved system of claim 1 wherein said system is a multi-lumen catheter.

6. The improved system of claim 1 further comprising electrical conductors running through the lumen of said catheter for delivery of electricity.

7. The improved system of claim 1 wherein said loop has a radius of curvature of at least 3/16".

8. The improved system of claim 7 wherein said catheter has an inner diameter of 0.104 inches and an outer diameter of 0.165 inches.

9. An improved system for the introduction of fluids or electrical leads to a patient, said system comprising:
   a percutaneous access device including a skirt for embedding in the subcutaneous tissue of the patient and a neck extending from the skirt for extending through the dermal and epidermal layers of the skin or the patient, said neck having a bore therethrough; and
   a catheter comprising at least two thermoplastic tubes each defining an internal lumen, each of said tubes having an outer diameter sized to permit insertion of the tube through said bore and having a proximal end for placement in the patient and a distal end located external to the patient when the catheter is in use, each of said tubes also having a permanent loop with an arc of at least 90° toward its distal end at a portion of the tube which is just external to the patient when the system is in place.

10. The improved system of claim 9 wherein said loop is heat-set.

11. The improved system of claim 9 wherein a remaining external portion of said tube, proximal to said external portion having said loop, may be oriented in any direction.

12. The improved system of claim 9 wherein said arc is at least 180°.

13. The improved system of claim 9 wherein said catheter is a multi-lumen catheter.

14. The improved system of claim 9 further comprising electrical conductors running through the lumen of said catheter for delivery of electricity.

15. The improved system of claim 9 wherein said loop has a radius of curvature of at least 3/16".

16. The improved system of claim 15 wherein said catheter has an inner diameter of 0.104 inches and an outer diameter of 0.165 inches.

17. An improved system for the introduction of fluids or electrical leads to a patient, said system comprising:
   a percutaneous access device including a skirt for embedding in the subcutaneous tissue of the patient and a neck extending from the skirt for extending through the dermal and epidermal layers of the skin of the patient, said neck having a bore therethrough; and a catheter comprising a thermoset tube defining an internal lumen, said tube having an outer diameter sized to permit insertion of the tube through said bore and having a proximal end for placement in the patient and a distal end located external to the patient when the catheter is in use, said tube also having a permanent loop with an arc of at least 90° toward its distal end at a portion of the catheter which is just external to the patient when the catheter is in place.

18. The improved system of claim 17 wherein said loop has a radius of curvature of at least 3/16".

19. The improved system of claim 17 wherein said catheter has an inner diameter of 0.104 inches and an outer diameter of 0.165 inches.

20. The improved system of claim 17 wherein said loop is heat-set.

21. The improved system of claim 17 wherein a remaining external portion of said tube, proximal to said external portion having said loop, may be oriented in any direction.

22. The improved system of claim 17 wherein said arc is at least 180°.

23. The improved system of claim 17 wherein said system is a multi-lumen catheter.

24. The improved system of claim 17 further comprising electrical conductors running through the lumen of said catheter for delivery of electricity.

25. An improved system for the introduction of fluids or electrical leads to a patient, said system comprising:

a percutaneous access device including a skirt for embedding in the subcutaneous tissue of the patient and a neck extending from the skirt for extending through the dermal and epidermal layers of the skin or the patient, said neck having a bore therethrough; and a catheter comprising at least two thermoset tubes each defining an internal lumen, each of said tubes having an outer diameter sized to permit insertion of the tube through said bore and having a proximal end for placement in the patient and a distal end located external to the patient when the catheter is in use, each of said tubes also having a permanent loop with an arc of at least 90° toward its distal end at a portion of the tube which is just external to the patient when the system is in place.

26. The improved system of claim 25 wherein said loop has a radius of curvature of at least 3/16".

27. The improved system of claim 23 wherein said catheter has an inner diameter of 0.104 inches and an outer diameter of 0.165 inches.

28. The improved system of claim 25 wherein said loop is heat-set.

29. The improved system of claim 25 wherein a remaining external portion of said tube, proximal to said external portion having said loop, may be oriented in any direction.

30. The improved system of claim 25 wherein said arc is at least 180°.

31. The improved system of claim 25 wherein said catheter is a multi-lumen catheter.

32. The improved system of claim 25 further comprising electrical conductors running through the lumen of said catheter for delivery of electricity.

* * * * *